United States Patent [19]

Elam

[11] 4,037,595

[45] July 26, 1977

[54] BREATHING EQUIPMENT SUCH AS RESUSCITATORS

[76] Inventor: James O. Elam, 950 E. 59th St., Chicago, Ill. 60637

[21] Appl. No.: 614,030

[22] Filed: Sept. 17, 1975

Related U.S. Application Data

[63] Continuation-in-part of Ser. No. 460,139, April 11, 1974.

[51] Int. Cl.² ............................................. A61M 16/00
[52] U.S. Cl. ................................... 128/145.7; 137/102
[58] Field of Search ......................... 128/145.5–145.8, 128/202, 203, 209, 210, 142.2; 137/102, 112, 539

[56] References Cited

U.S. PATENT DOCUMENTS

| | | | |
|---|---|---|---|
| 3,009,459 | 11/1961 | Ruben | 128/145.7 |
| 3,279,487 | 10/1966 | Elam | 137/102 |
| 3,473,529 | 10/1969 | Wallace | 128/145.7 |
| 3,474,785 | 10/1969 | Jansson | 128/145.7 |
| 3,827,451 | 8/1974 | Roob | 137/102 |
| 3,850,171 | 11/1974 | Ball et al. | 128/145.8 |

FOREIGN PATENT DOCUMENTS

| | | | |
|---|---|---|---|
| 1,175,514 | 8/1964 | Germany | 137/102 |
| 9583 | 1910 | United Kingdom | 128/209 |
| 903,179 | 8/1962 | United Kingdom | 137/539 |

*Primary Examiner*—Robert W. Michell
*Assistant Examiner*—Henry J. Recla
*Attorney, Agent, or Firm*—Synnestvedt & Lechner

[57] ABSTRACT

Breathing equipment, for instance a resuscitator, adapted to supply ambient air or alternatively oxygen from a pressurized source, the equipment including non-rebreathing valve mechanism having inspiration and expiration ports, and arranged to assure automatic operation to effect oxygen "blow-by" under conditions of operation tending to close the expiration port, and thereby prevent undesirable build-up of pressure in the patient's lungs.

1 Claim, 9 Drawing Figures

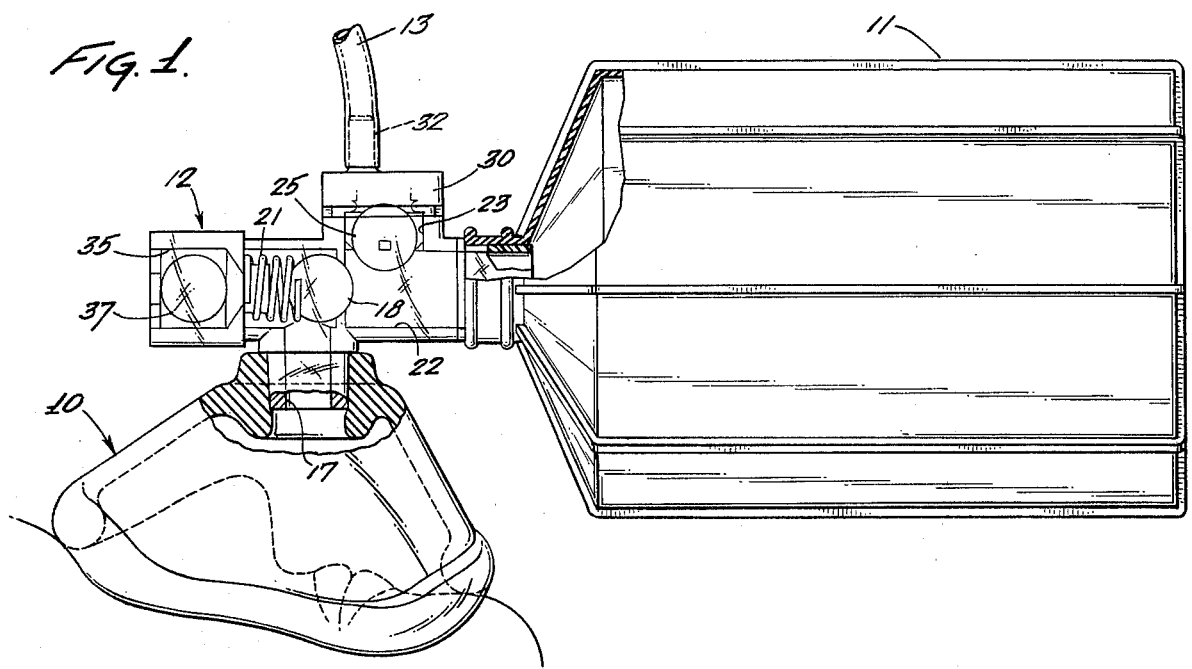
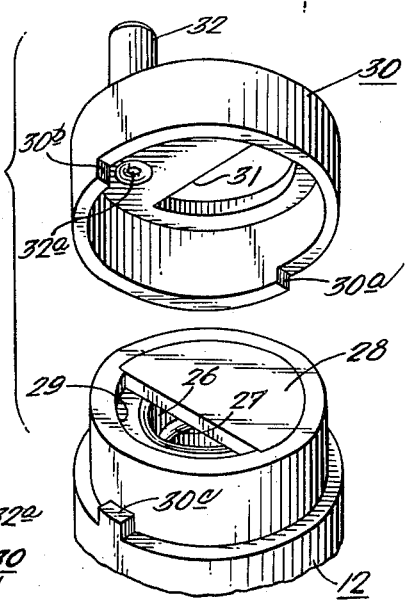
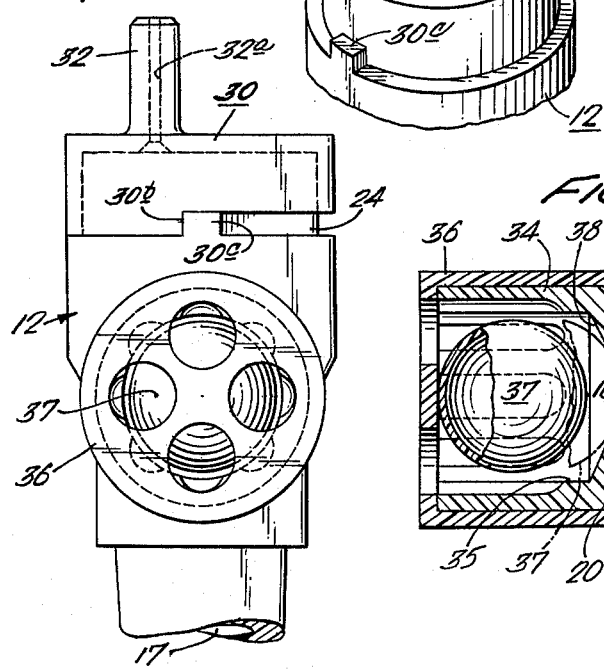
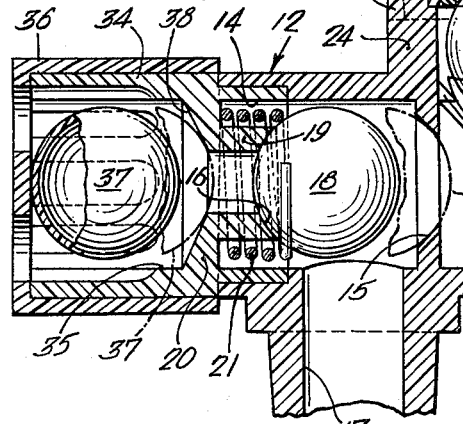
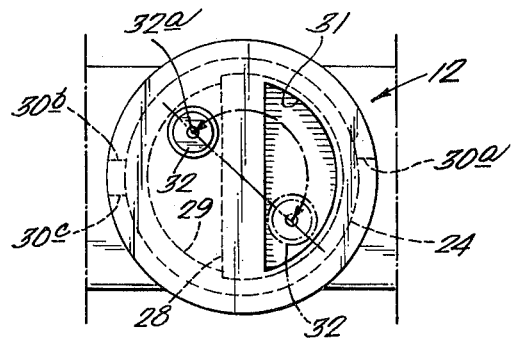
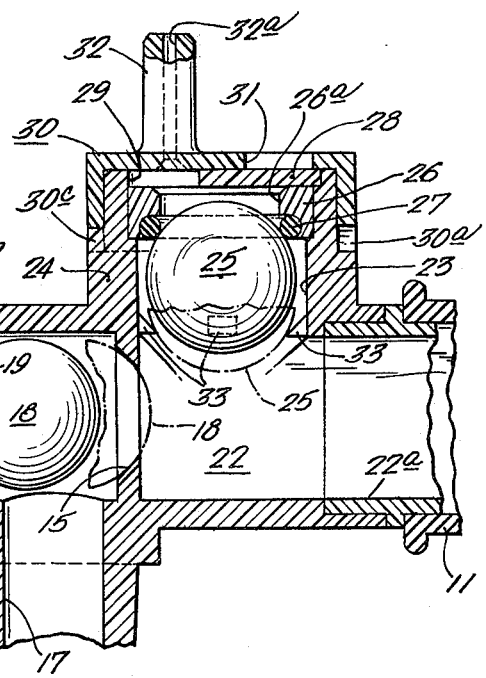

SPONTANEOUS EXPIRATION

SPONTANEOUS INSPIRATION

POSITIVE PRESSURE INSPIRATION

OXYGEN BLOW-BY

BREATHING EQUIPMENT SUCH AS RESUSCITATORS

CROSS REFERENCE

The present application is a continuation-in-part of my application Ser. No. 460,139 filed Apr. 11, 1974.

BACKGROUND AND STATEMENT OF OBJECTS

This invention relates to breathing equipment, particularly resuscitators, and the invention is especially concerned with a novel form of valve mechanism for such equipment. Although the arrangement of the invention is adapted for use in breathing equipment of a variety of types, it is particularly adapted for use in resuscitators of the kind employing a manual squeeze bag providing for temporary breathing assistance to patients who have temporarily and at least partially lost capability of spontaneous breathing. Since the invention is particularly useful in resuscitators, it is described and illustrated herein as used in a resuscitator.

It is customary in equipment of this general kind to provide alternatively for delivering either air or oxygen to the patient, or any desired admixture of air and oxygen. It is also customary in equipment of this kind to employ a valve mechanism which is of the so-called "non-rebreathing" type, i.e. valve mechanism which assures that the gases which are exhaled from the patient's lungs will not be returned to his lungs upon the next succeeding inspiration.

The equipment of the present invention provides for the attainment of all of the above functions and, in addition, overcomes certain difficulties and disadvantages of prior known equipment of this kind, especially the problem explained herebelow which has been encountered in various prior forms of equipment.

Thus, with various of the prior art devices, at times when substantial amounts of oxygen (including 100% oxygen) are supplied to the patient from the customary pressurized source (for example the emergency oxygen tank carried by an ambulance or rescue vehicle), there has been a tendency for the valve mechanism "to lock" in a position maintaining the flow path open through the valve mechanism from the pressurized source to the patient's lungs, while closing off the expiration port. If this condition is not quickly observed or recognized by the operator of the equipment and if steps are not taken to interrupt this continuous delivery of pressurized oxygen to the patient's lungs, serious injury to the patient may result.

It is a major objective of the present invention to provide automatic valve mechanism, resulting in automatic oxygen "blow-by", which virtually eliminates the hazards heretofore incident to defective equipment and/or operation thereof in a manner not adequately compensating for tendency for the valve mechanism to "lock" in the undesirable position above referred to.

At the same time, the arrangement of the present invention retains all of the other desirable functions above referred to and affords various other advantages hereinafter brought out in the following description.

BRIEF DESCRIPTION OF THE DRAWINGS

How the foregoing objects and advantages are attained, together with others which will occur to those skilled in the art will be understood from the following description referring to the accompanying drawings in which:

FIG. 1 is an elevational view, partially in section, showing a resuscitator arranged according to the present invention;

FIG. 2 is an enlarged longitudinal sectional view through the valve mechanism shown in FIG. 1;

FIG. 3 is an end elevational view thereof;

FIG. 4 is a fragmentary plan view of FIG. 2, illustrating further the air-oxygen mixing device;

FIG. 5 is an exploded perspective view illustrating more clearly certain details of FIG. 4.

DETAILED DESCRIPTION

Figure 6:
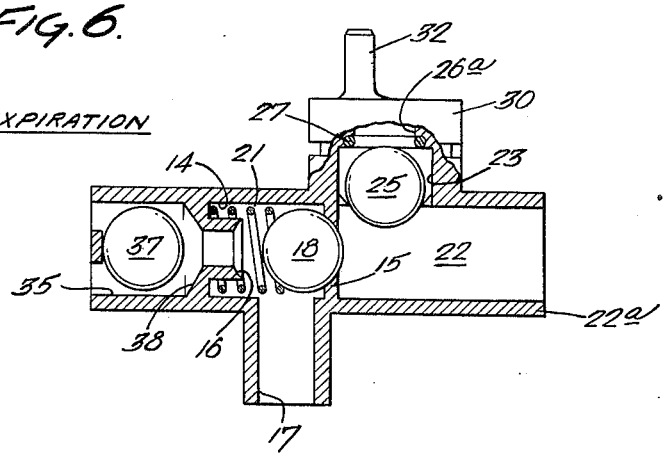
FIGS. 6 to 9 are diagrammatic views illustrating different positions of the valve parts, as assumed in response to different operating conditions.

The equipment generally illustrated in FIG. 1 includes a mask 10 adapted to be applied over the mouth and nose of the patient, the manual squeeze bag 11, and a valve mechanism generally indicated at 12 serving to interconnect the mask 10 and the squeeze bag 11. A supply line for pressurized gas, usually oxygen, is also indicated in FIG. 1 at 13.

It is to be understood that the equipment of the invention may be used not only with a mask such as shown in FIG. 1 but also in various other ways including with an endotracheal tube or esophageal obturator airway device.

In the central region of the valve mechanism 12 (see particularly FIG. 2), the valve mechanism is provided with a generally cylindrical chamber 14 and having at one end thereof an inspiration port and valve seat 15, and at the opposite end thereof an expiration port and valve seat 16. The chamber 14 further has a port in the side wall thereof indicated at 17 providing for communication with the mask 10 and thus with the patient's lungs.

A spherical or ball valve 18 is located in the chamber 14, this ball valve having clearance adjacent the side walls of the chamber and being movable in opposite directions to engage either of the valve seats 15 and 16 and thus to close one or the other of the inspiration and expiration ports.

When the ball valve 18 closes the inspiration port 15, an exhalation channel is provided through the side wall port 17, through the expiration port 16 to atmosphere, as will be explained hereinafter. When the ball valve 18 closes the expiration port 16, an inspiration channel is provided through the inspiration port 15 and the side wall port 17.

The expiration port and valve seat 16 is provided at the free end of a cylindrical boss 19 projecting from the end wall 20 of the chamber 14, and a spring 21, positioned by the boss 19, reacts between the end wall 20 and the ball valve 18, urging the ball valve to the right and serving to seat the ball valve on the inspiration valve seat 15 except in certain conditions of gas flow, as will be explained.

The valve mechanism 12 is provided with a chamber 22 for inspiration gases and with a connection 22a projecting toward the right as viewed in FIG. 1 and providing for attachment of the squeeze bag 11, so that air expelled from the bag by manually squeezing the bag will be delivered through the chamber 22 and through the inspiration port 15, this action resulting in displacement of the ball valve 18 to the left against the action of the spring 21.

The valve mechanism 12 has another chamber 23 projecting upwardly transversely of chamber 22, the chamber 23 being defined by the cylindrical wall 24 and housing a ball valve 25. This chamber 23 also receives the annular member 26, the central passage 26a of which forms the inlet passage for air or oxygen (or a mixture), a sealing ring, for instance an O-ring 27 being provided in position to cooperate with the ball valve 25, so that this valve may close off the passage 26a. An arcuate plate or element 28 (FIGS. 1 and 4) is positioned above the annular member 26, so as to leave an arcuate flow aperture indicated at 29 above the annular member 26, and a flanged cap or closure 30 having an arcuate aperture 31, overlies the element 28 and is rotative about the axis of the chamber 23 and passage 26a. The cap 30 is provided with a nipple 32 and having a central aperture 32a with which the oxygen supply tube 13 is associated. By rotating the cap 30 clockwise the aperture 31 may be brought more or less into registry with the aperture 29 thereby regulating the amount of air introduced through the passage 26a into the chamber 23. This rotative motion of the cap may also be used to bring the oxygen supply connection 32 into registry with the aperture 29 as shown in dotted lines in FIG. 4. Indeed by rotating the cap to different positions adjustment may be made to provide for admission of 100% oxygen or 100% air or any desired percentage intermixture.

By reference to FIGS. 4 and 5 respectively, it will be seen that the rim of the cap 30 is provided with circumferentially spaced shoulders 30a and 30b adapted to engage a stop lug 30c on the cylindrical wall 24 in order to limit the rotation of the cap. In FIG. 4 the cap has been rotated counterclockwise an amount such that the shoulder 30b has engaged the stop lug 30c, thus adjusting apertures 31 and 29 to preclude admission of air to chamber 23 as clearly shown in FIG. 2. This is the position in which air is fully cut off and in which 100% oxygen will be supplied through the inlet passage 32a. It will be seen that clockwise rotation of the cap 30 from this position will progressively diminish the oxygen inflow and will bring apertures 31 and 29 into varying degrees of overlap to provide the admission of the desired air/oxygen mixture, and also provide for 100% air inflow, as previously set forth.

The ball valve 25 is provided with clearance adjacent the surrounding wall 24, and this ball valve is retained in position close to the sealing ring 27 by means of circumferentially spaced fingers or tabs 33 (see FIGS. 2 and 4).

Referring again to FIGS. 2 and 3, it will be seen that at the left of the valve mechanism 12, an extension 34 is provided, defining a general cylindrical chamber 35 the left hand end of which is provided with an apertured cover 36. This chamber receives a ball valve 37 having clearance at its periphery and serving to engage the seat 38 surrounding the expiration passage which extends through wall 20 of the chamber 14 and through the nipple 19. It will be observed that the expiration chamber 35 is always in communication with atmosphere at the left hand end of the valve mechanism 12.

The ball valves 25 and 37 are in effect one way check valves and need not necessarily be ball valves. However, since it is contemplated according to the present invention that valve 18 shall be a spherical or ball valve, it is convenient and desirable to standardize on the use of ball valves. Indeed according to the preferred embodiment of the invention, all of these ball valves are identical and may freely be interchanged in manufacturing and servicing. The valve balls are desirably formed of resin or plastic material such as polypropylene and may be either solid or hollow. Light weight metal such as aluminum may also be employed for hollow valve balls. Most advantageously, for the purpose of the present invention the ball valve 18 should be quite light in weight, for instance a hollow, relatively thin walled sphere of polypropylene.

It is also contemplated according to the invention that the various parts of the valve mechanism 12 is formed of transparent resins or plastic material, for instance polypropylene, it being contemplated that in the preferred embodiment, the valves should be clearly visible through the walls of the valve housing, and for this purpose it is even preferred to employ ball valves which are pigmented or otherwise colored so as to be readily visible through the walls of the various valve chambers as is indicated in FIG. 1.

Turning now to the diagrammatic views of FIGS. 6 to 9 inclusive, it will be seen that each one of these views has been labeled to indicate the operating condition represented in that view. Thus, FIG. 6 represents a condition of "Spontaneous Expiration" by the patient. In this view the valve 18 has been moved by the spring 21 to a position closing the inspiration port 15, and the expiration valve 37 has been displaced from the seat 38 of the expiration passage. A channel is thus formed from the mask connection 17 past the ball valve 18 and through the expiration port to atmosphere at the left end of the valve mechanism. At this time the check valve 25 at the intake side is inactive as is also the squeeze bag which is associated with the connection 22a.

Figure 7:
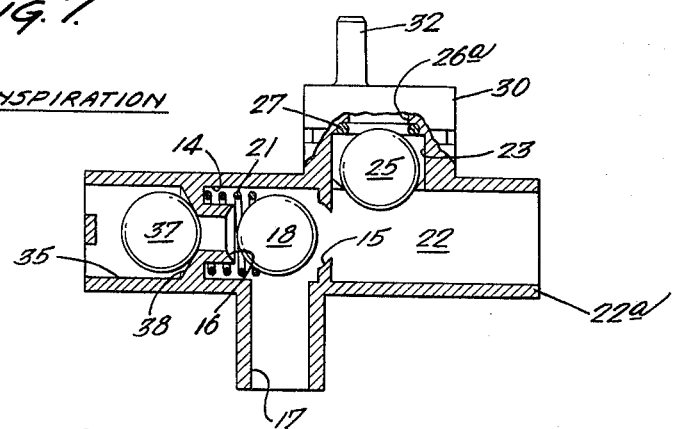

In FIG. 7 the condition of "Spontaneous Inspiration" is illustrated. Here it will be seen that the ball valve 18 is moved somewhat to the left against the action of the spring 21, thereby opening the inspiration port 15 so that the patient may draw air or oxygen or a mixture, from the various passages and chambers to the right of the inspiration port 15 past the valve 18, and through the connection 17 to the patient. This inspiration will also result in movement of the valve 37 against the seat 38 around the expiration port, thereby preventing inspiration of gases from the left hand end of the valve mechanism.

Figure 8:
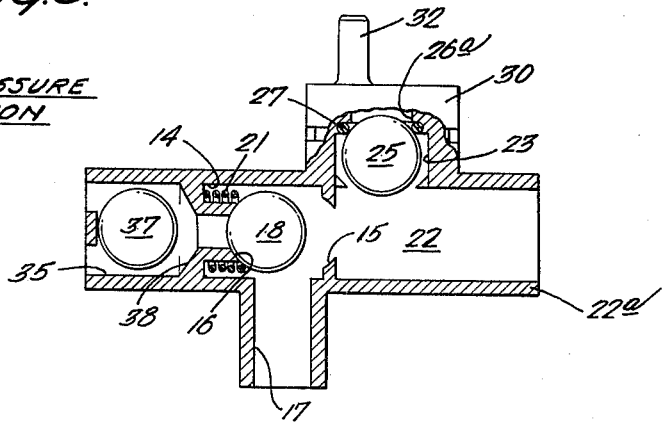

FIG. 8 illustrates the condition of "Positive Pressure Inspiration". This assumes that the attendant or operator of the equipment is effecting a definite or positive squeezing of the squeeze bag which is associated with the connection 22a, thereby causing the check valve 25 to move upwardly and close off the intake by engagement with the seat or seal 27. In addition this action also forces the valve 18 to the left against the action of the spring 21 and causes this valve to close the expiration port 16, and thus result in delivery of inhalation gas (air and/or oxygen) from the squeeze bag into the patient's lungs. In this condition of operation the check valve 37 at the expiration side remains idle.

Figure 9:
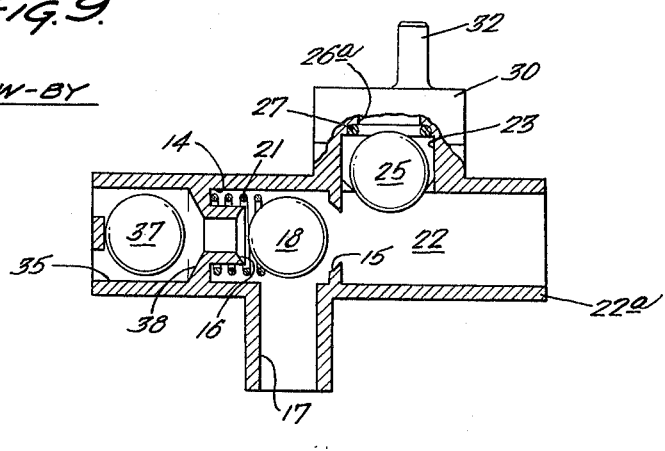

In FIG. 9 there is illustrated a condition of operation herein referred to as "Oxygen Blow-by". For purposes of explanation, it is assumed that the cap 30 over the intake chamber is adjusted so as to provide 100% oxygen delivery into the chamber 22. In other words it is here assumed that the cap is adjusted so as to close the air admission passage 31 and deliver oxygen only into the intake chamber. It is further assumed in connection with FIG. 9 that the squeeze bag which is associated with the connection 22a, remains idle. These conditions correspond with those in which certain prior equipment has resulted in valve operation tending to undesirably build up pressure in the patient's lungs. Thus, with certain prior devices, the valve employed for the purpose of establishing the "non-breathing" type of operation, i.e., the valve employed in certain prior devices in the position of the ball valve 18 herein disclosed, tended to "lock" in a position in which the expiration port 16 was completely closed off.

In the arrangement herein described and illustrated however, such "locking" of the "non-rebreathing" valve will not occur in the conditions referred to, even when the supply of oxygen being delivered from the pressurized supply tank corresponds to the maximum oxygen flow required by an adult, i.e., about 25 liters per minute. Moreover, with the arrangement as herein disclosed, the oxygen feed rate may even be increased 8 to 12 liters per minute above the maximum normal requirement, i.e. as much as 50% excess, without resulting in "locking" of the rebreathing valve in the position in which the expiration passage is closed.

In consequence of this operating characteristic, as shown in FIG. 9, the valve 18, although displaced from the inspiration port 15, is not engaged with the expiration port 16, and under the conditions described, excess oxygen will "blow-by" i.e., will pass to atmosphere through the expiration passage and thus will prevent abnormal and undesired pressure build up in the patient's lungs.

There are several features of importance in applicant's equipment which assure the capability of "blow-by" operation under the potentially hazardous conditions above referred to. One of the distinctive features accomplishing this important objective is the use of a spherical or ball valve in the position of the "non-rebreathing" valve, which is not only important because of its shape, but also because it is, in effect a free floating valve element, rather than an element subjected to positive guiding action, as in the case of a valve mounted by a valve stem or on a spindle. Another of the distinctive features is the use of a spring for urging the valve 18 toward the inspiration port 15, which spring is of special characteristics and configuration as will be explained. Still further, the relative proportions of the inspiration and expiration ports as disclosed herein is also of importance.

The use of a spherical light weight ball, instead of a flat disc shaped valve, for the non-rebreathing valve, particularly where the cross sectional area of the inspiration port is substantially larger than the cross sectional area of the expiration port, has a tendency, because of a Bernoulli type effect to retain the ball at a location somewhat separated from the expiration port, at times when the steady flow of oxygen from a pressurized supply source is entering the equipment and flowing through the inspiration port 15 and around the spherical valve 18.

With this type of operation in mind, it is preferred that the cross sectional area of the inspiration port should be at least two times the cross sectional area of the expiration port. It is also preferred that the expiration port be centered in the mid region of the chamber in which the ball valve 18 is mounted, which is accomplished in the embodiment illustrated by locating the expiration port centrally of nipple 19, rather than in an annulus surrounding that nipple, or in some other relationship to the axis or path of motion of the non-rebreathing valve between the inspiration port and the expiration port.

In the practice of the invention, it is contemplated that the spring employed in association with the ball valve 18 should of course be deflectable through a sufficient range to provide for engagement of the valve with the inspiration seat and also for engagement of the valve with the expiration seat. This spring moreover is also preferably proportioned to have a total deflection range from zero deflection to maximum deflection, which range is only slightly greater than that corresponding to the total range of valve movement from its position of engagement with the inspiration port seat and its position of engagement with the expiration port seat. Stated in another way, the spring 21 if removed and released from the equipment would expand only slightly beyond the extent of expansion which will occur with the spring in position and expanded to move the ball valve against the inspiration port seat. Because of this proportioning of the spring in relation to the extent of valve motion, for a predetermined force of engagement of the valve with the inspiration valve seat, the resistance to deflection (i.e. to compression) of the spring increases much more rapidly with the spring proportioned according to the invention, than in the case where the total range of available deflection of the spring is much greater than the length of the path of movement of the valve.

In the preferred embodiment, the spring 21 comprises a helical compression spring having only a few turns, for instance 3 to 8 turns, and the spring is advantageously formed of plastic or resin material such as nylon, although some metals such as stainless steel may be used. The total available range of deflection of the spring is advantageously not more than about 150% of the extent of movement of the valve, most desirably not more than about 110% to 120% of the valve movement. As shown, one end of the spring is accommodated in an annular recess surrounding the expiratory flow path just downstream of the expiration port.

The spring is also advantageously anchored at the bottom of the annular recess, for instance by attaching a washer to the end of the spring, the washer snugly fitting in the annular recess. In this way, the spring will not be lost when the valve structure is taken apart for cleaning or for replacement of valve balls.

The equipment of the present invention includes still another feature for preventing excessive build up of pressure in the patient's lungs. This feature comprises the employment of a nipple 32 for attachment of the oxygen supply tube, which nipple is provided with a smooth external and preferably straight (i.e. non-tapered) surface as shown, so that the oxygen supply tube 13 will be forcibly detached or separated from the nipple upon abnormal build up of pressure upstream of the nipple. The nipple is provided with a restricted flow passage 32a, for example a flow passage of from about 0.02 to about 0.04 inches in diameter, for example about 0.04 inch. This restricted flow passage is also of some appreciable length, preferably from between about 0.75 inch to about 1.25 inches, for example about 1 inch in length.

With the attachment nipple constructed in this manner, and with an oxygen supply tube having normal frictional fit, the oxygen supply tube will be blown off the nipple if the rate of feed of oxygen to the nipple exceeds about 25 liters per minute, which, as above indicated, represents the maximum normal adult requirement.

In accordance with the invention, the arrangement of the oxygen tube attachment nipple and the arrangement of the non-rebreathing valve including the valve ports, ball valve and spring features above described, cooperate in preventing build up of excessive pressure in the patient's lungs when the equipment is connected with a source of oxygen under pressure. Thus, the valve arrangement (port sizes, ball valve and spring features) prevent "locking" of the valve at oxygen inflow rates up to about 25 liters per minute, and the arrangement of the oxygen tube attachment nipple (with normally sized supply tube) provides a safety factor preventing valve lock for oxygen flow rates in excess of 25 liters per minute.

In connection with the arrangement of the attachment nipple referred to above, it is to be kept in mind that in oxygen supply equipment employed for hospital and emergency purposes, an oxygen flow meter is ordinarily provided including a valve, such as a needle valve for regulating the quantity of oxygen being supplied. The maximum output provided by such equipment with the control valve wide open, ranges from about 30 to about 60 liters per minute. The provision of the oxygen supply nipple, with its restricted passage and smooth surface provides an additional safeguard against the use of the breathing equipment in a manner in which the flow rate of oxygen through the non-rebreathing valve appreciably exceeds that at which the non-rebreathing valve will close the expiration port, i.e. a flow rate on the order of about 25 liters per minute. At rates substantially above about 25 liters per minute, the oxygen tube will be blown off.

As a further safeguard the attachment nipple may be proportioned to forcibly detach the oxygen supply tube at a flow rate somewhat below the maximum value at which the non-rebreathing valve will normally prevent valve locking. For instance if the non-rebreathing valve will normally prevent locking up to a flow rate of 25 liters per minute, the tube attachment nipple may be proportioned to normally separate at a flow rate of about 20 liters per minute.

It is advantageous to provide the restricted flow passage 32a in the nipple 32 because this location is conveniently accessible to the operator, and the "pop" occurring upon tube detachment will readily be heard by the operator, who is thereby warned that the oxygen flow rate should be reduced by adjustment of the regulator or flow meter.

I claim:

1. A resuscitator valve mechanism including a valve chamber having opposed inspiration and expiration ports in opposite ends thereof each having a valve seat surrounding the port, and the chamber having a port in a side wall of said chamber between the ends thereof for communication with the patient's lungs, a light weight ball valve in said chamber having clearance for gas flow around the valve adjacent the side walls of the chamber and being movable in opposite directions to engage either of the valve seats and close one or the other of the opposed ports, a compression spring between the ball valve and the wall of the valve chamber around the expiration port and urging the ball valve away from the expiration port seat, and the valve mechanism having means providing for connection of a source of pressurized inspiration gas and for directing such pressurized gas to the inspiration port, the ball valve being movable away from the inspiration valve seat under the influence of the pressurized gas, and said spring being deflectable sufficiently to provide for engagement of the ball valve with the expiration port seat and thus close the expiration port, the expiration port being centrally located at one end of said chamber and having a cross sectional area substantially smaller than the inspiration port thereby tending to retain the ball valve in a position spaced from the expiration port during selected flows of inspiration gas from a pressurized source thereof connected with the valve mechanism, and the spring being a helical coil spring having an inside diameter at least as large as the expiration port and having one end seated against the end of the valve chamber in an area surrounding the expiration port and the other end presented for engagement with the ball valve, and the motion of the light weight ball valve in said valve chamber being unguided except for the action of said spring and of the gas flow through the valve chamber.

* * * * *